(12) United States Patent
Alamry et al.

(10) Patent No.: US 11,491,199 B1
(45) Date of Patent: Nov. 8, 2022

(54) **ANTICOAGULATION ACTIVITY OF SULFATED CARBOXYMETHYL CELLULOSE/*AZADIRACHTA INDICA* LEAF POWDER-BASED BIOCOMPOSITES**

(71) Applicant: King Abdulaziz University, Jeddah (SA)

(72) Inventors: Khalid A. Alamry, Jeddah (SA); Ajahar Khan, Jeddah (SA); Mahmoud A. Hussein, Jeddah (SA); Abdullah M. Asiri, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 17/342,593

(22) Filed: Jun. 9, 2021

(51) Int. Cl.
*A61K 36/58* (2006.01)
*A61K 47/52* (2017.01)
*A61P 7/02* (2006.01)
*A61K 47/61* (2017.01)

(52) U.S. Cl.
CPC .............. *A61K 36/58* (2013.01); *A61K 47/52* (2017.08); *A61K 47/61* (2017.08); *A61P 7/02* (2018.01)

(58) Field of Classification Search
CPC ........ A61K 36/58; A61K 47/52; A61K 47/61; A61P 7/02
See application file for complete search history.

(56) References Cited

U.S. PATENT DOCUMENTS 3,980,772 A * 9/1976 Ginger ................. A61K 38/166
424/94.3
2009/0227537 A1 9/2009 Grady et al.
2009/0263466 A1* 10/2009 Managoli ................ A61P 25/22
424/456

OTHER PUBLICATIONS

Neem Foundation (2014).*
Alamry et al. (Published online Jan. 30, 2021).*
Fan et al., "Preparation of carboxymethyl cellulose sulfates and its application as anticoagulant and wound dressing", Int J Biol Macromol, May 2014;66:245-53, Abstract.
Hossain et al., "Molecular docking and ADME/T analysis for identification of novel potential COX inhibitors of some isolated compounds from Azadirachta indica for Thrombolytic treatment", International Journal of Advanced Scientific Research, vol. 3; Issue 1; Jan. 2018; p. 29-31.
Hussain et al., "In vitro thrombolytic potential of root extracts of four medicinal plants available in Bangladesh", Anc Sci Life. Jan.-Mar. 2014; 33(3): 162-164.
S. Islam, "Antimicrobial and Thrombolytic Activities of Decoction of Azadirachta indica", SEU Journal of Science and Engineering, vol. 13, No. 1, Jun. 2019.
Khan et al., "Thrombolytic potential of *Ocimum sanctum* L., *Curcuma longa* L., *Azadirachta indica* L. and *Anacardium occidentale* L.", Journal of Basic and Clinical Pharmacy, Jun. 2011-Aug. 2011; 2(3): 125-127.

* cited by examiner

*Primary Examiner* — Shirley V Gembeh
(74) *Attorney, Agent, or Firm* — WC&F IP (57) ABSTRACT

Biocomposites comprising sulfated carboxymethyl cellulose and *Azadirachta indica* leaf extracts are provided. The sulfated carboxymethyl cellulose is made using an improved, environmentally friendly technique. Methods of using the biocomposites as anticoagulants are also provided.

6 Claims, 6 Drawing Sheets

ANTICOAGULATION ACTIVITY OF SULFATED CARBOXYMETHYL CELLULOSE/*AZADIRACHTA INDICA* LEAF POWDER-BASED BIOCOMPOSITES

BACKGROUND OF THE INVENTION

Field of the Invention

The invention generally relates to biocomposites comprising sulfated carboxymethyl cellulose and *Azadirachta indica* leaf extracts. In particular, the sulfated carboxymethyl cellulose is made using an improved environmentally friendly technique, and methods of using the biocomposites as anticoagulants are provided.

Description of Related Art

In the present time with the advancement of technology in the field of clinical science, various types of biomaterials such as ceramics, metallic components, composite materials and natural or synthetic polymers have been employed for a variety of medical applications. Over time, the number of these biomaterials has expanded to fulfill the demand of clinical needs on both the therapeutic and diagnostic fronts [1]. The characteristic features of natural and synthetic materials that are used clinically, e.g. as anticoagulants where they make direct contact with blood, are essential to obtaining satisfactory results e.g. for grafts, implants, etc. Physiologically adequate biomaterial/blood agreement is vital for blood-contacting biomaterials.

At the time of blood clotting, plasma proteins (primarily fibrinogen, globulin, serum albumin and prothrombin) are rapidly absorbed on the surface of solid materials (e.g. a foreign body such as an implant), which stimulates platelets and causes their aggregation and adhesion for blood clotting [2]. Heparin, which is made up of sulfated polysaccharide backbones comprising repeating units of D-glucosamine and either D-glucuronic or L-iduronic acids [3], is a naturally occurring and widely used anticoagulant. The presence of carboxylate, sulfamide and sulfate based ionic functional groups are the key factors of heparin's anticoagulant activity. They help to immobilize heparin onto material and improve blood compatibility via ionic bonding and/or physical absorption [4-7]. For many decades, the heparin has been the main choice for the treatment and prevention of thromboembolic disorders. However, some problems related to clinical applications of heparin have also been reported. For example, its inadequacy for antithrombin deficient patients, and serious side effects such as the release of immobilized heparin into the blood, which results in abnormal blood flow, tissue hemorrhage and thrombocytopenia [8,9].

Other natural or chemically synthesized sulfated polysaccharides also possess anticoagulant activity and blood compatibility [10,11]. Cellulose derivatives such as carboxymethyl cellulose (CMC), obtained in large quantities through the treatment of cellulose with sodium monochloroacetate in the presence of sodium hydroxide, is used for a variety of applications, including detergents, papers, flocculation, textiles, fand ood and drug release [12,13]. The existence of many carboxy methyl groups ($-CH_2COO^-$) in CMC appears to enhance its water solubility [14,15]. Moreover, after sulfation, CMC has also possessed a high level of blood compatibility because of the similarity in the structure with that of heparin.

Among different types of biomaterials, plant extracts have achieved modest consideration owing to their ready availability, low cost and eco-friendly nature. *Azadirachta indica* (*A. indica*), which belongs to family Meliaceae, is an evergreen and indigenous plant widely available in India and southeast countries. This plant has promising potential towards ayurvedic therapeutics owing to its remedial properties with proven ant-inflammatory, antiviral, antidiabetic, antifungal, skin healing, anti-ulcer and antiretroviral activities [16-18]. Moreover, water soluble leaf extracts of *A. indica* also possess antifertility, antiserotonin, hypotensive, hypoglycemic, and hepatoprotective activity [19]. Researchers have shown that *Azadirachta indica* extracts include several types of compounds, a wide range of which have pharmacological potential. Triterpenes lead the way in having therapeutic applications and Nimbin (triterpene) has been shown to have antiseptic, antihistamine, fungicidal and antipyretic properties. Nimbin also exhibits antioxidant and anti-inflammatory activities, decreasing cellular damage by mitigating the formation of oxygen reactive species [20,21]. Flavonoids are also found in *A indica* and function as inhibitors of prostaglandin biosynthesis, phosphodiesterases, endoperoxides and other enzymes such as protein kinases, which are concerned with inflammation [21-23]. On the other hand, oil extracts of *Azadirachta indica* contain large amounts of saponins, flavonoids, and triterpenes while other components for instance nimbins, and catechins appear to be present in lower amounts [20,21]. Other metabolites present in *A. indica* extracts include: alkaloids, limonoids, tannins, gallic acid, sterols, catechins, terpenoids and reducing sugars [20,21,24,25]. The leaf of *A. indica* seems to have developed a specific set of glycoproteins that when tested in mammals, exhibited immune-modulatory activity, and inhibiting tumor by modulating systemic and local immunity [26-29]. Leaf extracts of *A. indica* also contain high levels of glycosides, tannins, saponins, flavonoids, and alkaloids [30]. The effects that are seen when using *A. indica* extracts are attributed to cellular and molecular mechanisms, including detoxification, free radical scavenging, DNA repair, immune surveillance, programmed autophagy and cell death mitigation, cell cycle alteration, anti-inflammatory, anti-metastatic and anti-angiogenic activities and the capability to modulate various signaling pathways [31,32].

Reactive oxygen and free radical's species of *A. indica* are also sources of inflammation, exerting injury by taking removing electrons and unleashing in the cell a condition of oxidative stress [34,35]. Thus, there is a need to provide suitable compounds such as polymers or fillers to neutralize or stabilize these radicals and block and prevent an exacerbation of oxidative stress, while still obtaining the medicinal benefits of the other compounds that are found in *A. indica*.

SUMMARY OF THE INVENTION

Considering the importance of green processing and taking into account the significance of S-CMC and the medicinal benefits of NLP, the present disclosure describes the fabrication of cost effective and eco-friendly biocomposites based on sulfated-carboxymethyl cellulose (S-CMC) and *A. indica* leaf (NLP) extracts using a simple and environmentally friendly "green" chemical approach. The S-CMC/NLP based biocomposites were examined by X-Ray diffraction (XRD), UV-Vis spectroscopy, FT-IR, FE-SEM and EDAX analysis and were also analyzed to investigate their anticoagulant effect. The results obtained for partial thromboplastin time (PT) and activated partial thromboplastin time (APTT) assays showed that the newly fabricated S-CMC/

NLP based biocomposites can be used beneficially in chemical pharmaceutical and clinical applications.

The modified sodium carboxymethyl cellulose sulfates were prepared with a sulfating agent $(N(SO_3Na)_3)$ using sodium nitrite and sodium bisulfite by a novel method which is also described herein. Conventionally, sulfation is carried out by utilizing sulfuryl chloride, sulfuric acid, sulfur trioxide, sulfamic acid and chlorosulfonic acid. These sulfating agents not only result in intense degradation of polysacharide polymer backbones, but also cause severe pollution problems [33]. Compared with conventional techniques, the fabrication methods described herein were advantageously accomplished in aqueous media. Moreover, the prepared sulfating agent utilized for the sulfation of CMC is non-toxic and cost effective to produce.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

It is an object of this invention to provide a biocomposite comprising *Azadirachta indica* leaf powder crosslinked to sulfated carboxymethyl cellulose (S-CMC). In some aspects, the level of sulfation of the S-CMC is 10 to 15%, w/v. In further aspects, the ratio of *Azadirachta indica* leaf powder to sulfated carboxymethyl cellulose (S-CMC) is from 0.5 to 1.5.

Also provided is a method of dissolving blood clots in a subject in need thereof, comprising administering to the subject a therapeutically effective amount of a biocomposite comprising *Azadirachta indica* leaf powder crosslinked to S-CMC. In some aspects, the therapeutically effective amount ranges from 0.04 to 0.2. In further aspects, the subject suffers from myocardial infarction, thromboembolic strokes, deep vein thrombosis, atrial fibriallation and/or pulmonary embolism.

Also provided is a method of making a biocomposite, comprising forming a suspension *Azadirachta indica* leaf powder and S-CMC in an aqueous medium, and crosslinking the *A. indica* leaf powder and the S-CMC. In some aspects, the quantity of *A. indica* leaf powder in the suspension is 5-20% wt/vol. In further aspects, the quantity of S-CMC in the suspension is 1-10% wt/vol. In additional aspects, prior to the step of forming, the S-CMC is made by reacting CMC and $(N(SO_3Na)_3)$ in an aqueous medium. And in yet further aspects, the $(N(SO_3Na)_3)$ is made by reacting sodium nitrite and sodium bisulfate in an aqueous medium. In some aspects, the aqueous medium is double distilled water (DDW). In other aspects, the aqueous medium is double distilled water (DDW). In additional aspects, the aqueous medium is double distilled water (DDW).

DETAILED DESCRIPTION

Biocomposites based on sulfated-carboxymethyl cellulose (S-CMC) and *A. indica* leaf (NLP) extracts are described herein, as are methods of making and using the biocomposites.

Making the Biocomposites

The disclosed biocomposites are made from powdered *A. indica* (neem) leaves and carboxymethyl cellulose (CMC) that has been sulfated.

*Azadirachta indica*, commonly known as neem, nimtree or Indian lilac, is a tree in the mahogany family Meliaceae. *A. indica* is native to the Indian subcontinent and is typically grown in tropical and semi-tropical regions but is also grown in Saudi Arabia. To practice the present invention, fresh *A. indica* leaves are gathered, washed and dried before being ground into a fine powder. For example, several washes with water, such as distilled water (DDW) three times, and drying for 1-3 days or more at e.g. about 35 to 50° C., such as about 40° C. suffices to prepare the leaves for grinding using any suitable method (e.g. by hand using a mortar and pestle, using a blender, using mechanical rollers, etc.). After a fine powder is obtained, it is typically washed e.g. with water, acetone, or other suitable solvents to remove impurities and then dried, e.g. at ambient or elevated temperatures e.g. from about 25° C. to about 40° C.

Alternatively, commercial sources of purified powdered *A. indica* leaves are also known and may be used.

Carboxymethyl cellulose (CMC) or "cellulose gum" is a cellulose derivative with carboxymethyl groups ($—CH_2—COOH$) bound to some of the hydroxyl groups of the glucopyranose monomers that make up the cellulose backbone. It is often used as its sodium salt (sodium carboxymethyl cellulose). CMC can be synthesized by the alkali-catalyzed reaction of cellulose with chloroacetic acid. The polar carboxyl groups render the cellulose soluble and chemically reactive. Following the initial reaction, the resultant mixture produces about 60% CMC plus 40% salts (sodium chloride and sodium glycolate). This product is the so-called technical CMC which is used in detergents. A further purification process is used to remove these salts to produce the pure CMC used for food, pharmaceutical, and dentifrice (toothpaste) applications. An intermediate "semi-purified" grade is also produced, typically used in paper applications such as restoration of archival documents. For making the biocomposites disclosed herein, highly purified, food grade CMC is utilized. Highly purified CMC is commercially available.

For use in making the biocomposites disclosed herein, the CMC is sulfated. The present invention advantageously uses a special sulfating agent, $(N(SO_3Na)_3)$, the making and use of which are environmentally friendly. $(N(SO_3Na)_3)$ is prepared from sodium nitrite and sodium bisulfate. As an example, to make 100 ml of the reagent, 0.1 M sodium bisulfate is dissolved in 80 mL DDW in a suitable reaction vessel and 20 ml of 1 M sodium nitrite (in DDW) is slowly added to the vessel, dropwise over a period of time ranging from at least about 30 minutes to about 2 hours, such as about 30, 60, 90 or 120 minutes. The addition is generally performed with constant agitation at an elevated temperature (e.g. about 80 to 95° C., such as about 80, 85, 90, or 95° C. 90° C. At the end of this time, $(N(SO_3Na)_3)$ is formed. Prior to use as a CMC sulfating agent, the pH of the $(N(SO_3Na)_3)$ is adjusted to ~8 (e.g. using a suitable base such as 0.2 M NaOH).

In some aspects, formation of sulfated CMC is performed in the same reaction vessel, e.g. by adding CMC directly to the pH adjusted $(N(SO_3Na)_3)$. As an example, 10 g of solid CMC is added slowly to the pH adjusted $(N(SO_3Na)_3)$ while being agitated, e.g. with strong mechanical agitation (600 rpm). Once the CMC has been added, the reaction is allowed to proceed for about 2.5 to about 10 hours, such as about 5 hr, at a temperature in the range of from about 35-55° C., such as about 45° C. temperature. Sulfated CMC (S-CMC) forms as a viscous gel formed which is then dried (e.g. at about 40-60° C., such as about 50° C.) to completely evaporate the solvents. The dried S-CMC is thoroughly washed (e.g. with DDW and acetone or other suitable solvent) and then completely dried, e.g. at about 50-70° C., such as at about 60° C.

In some aspects, a solution casting method is used to fabricate the S-CMC/NLP biocomposites. For example, a desired concentration of *A. indica* leaf powder (NLP) (e.g. from about 1 to about 10% wt/vol or higher, such as about 2.5%, 5.0% or 7.5% (w/v)) is mixed with a quantity of DDW sufficient to suspend the powder, e.g. as a slurry, suspension or dispersion, with constant stirring for e.g. about 2.5 to 10 hours, such as about 5 h, at a temperature of from about 40-50° C., such as about 45° C. The resulting mixture is then sonicated e.g. for about 30 to 90 minutes, such as for about 60 minutes. Dried S-CMC (e.g. from about 1-10% w/v, such as about 5% w/v) is then added to the NLP solution with constant stirring at a temperature of from about 40-50° C., such as about 45° C. Sufficient gluteraldehayde is added to the solution and the reaction is allowed to proceed with strong mechanical agitation (e.g. at least 500 rpm) for a period of time ranging from about 24 to 48 hours, such as about 36 h, at a temperature of from about 40-50° C., such as about 45° C. As is known to those of skill in the art, glutaraldehyde acts as an amine-reactive homobifunctional crosslinker and thus crosslinks the NLP molecules to the S-CMC and may also cause the formation of cross-links within the NLP and/or the S-CMC itself. After this, the reaction mixture is sonicated for from about 2.5 to about 4.5 hours, such as about 3.5 h. The results is a gel. The resulting S-CMC/NLP biocomposite mixture is cast into a suitable mold or container and completely dried, e.g. at about 50-70° C., such as about 60° C., for from about 1-24 hours. Lastly, the dried S-CMC/NLP composite is washed e.g. for 1-2 hrs with a suitable, non-reactive solvent that quickly evaporates (a highly volatile solvent such as acetone) and crushed into a fine powder of a desired fineness by any suitable means. For example, a mortar and pestle may be used, or mechanical shearing device (e.g. a blender), rollers that crush the material, etc.

Those of skill in the art will recognize that in these synthesis steps, washes with acetone may be replaced by washes with other solvents such as methyl acetate or commercially available "green" and/or biodegradable acetone replacements such as Surfasolve, Bio-Solv, Replacetone™, etc., as long as the solvent does not leach or dissolve the active ingredients from the product that is being washed.

The Biocomposites

The biocomposites disclosed herein comprise sulfated CMC (S-CMC) and NLP. The S-CMC portion of the biocomposite generally has a level of sulfation in the range of from about 5-20%, such as about 5, 6, 7, 8, 9, 10, 11, 12, 13, 14, 15, 16, 17, 18, 19, or 20%. In some aspects, the level of sulfation is about 10 to 15%, such as about 12%. The amount of S-CMC may be increased (or decreased), based on calculations of the degree of sulfated content.

The amount of NLP in the biocomposites generally ranges from about 1.0 to about 10% w/v, prior to the last step of drying. For example, the amount prior to the last step of drying is generally about 1, 2, 3, 4, 5, 6, 7, 8, 9, or 10% w/v, depending on the desired strength of activity (see below under "USES").

After the final product is dried and ready for use, the amount of NLP in the biocomposite, on a w/v basis, generally ranges from about 2.5% to about 7.5%. After the final product is dried and ready for use, the amount of S-CMC in the biocomposite, on a w/v basis, generally ranges from about 1% to 10%, or about 2.5 to 7.5%, e.g. about 5%. Generally, the ratio of *Azadirachta indica* leaf powder to S-CMC in the biocomposite, both before and after drying, is from about 0.05 to 10, such as about 0.1 to 5, e.g. about 0.5 to 1.5.

Administration of the Biocomposites

The biocomposites described herein are generally delivered (administered) as a pharmaceutical composition. Accordingly, the present invention encompasses such formulations/compositions. The compositions generally include a substantially purified form of a biocomposite as described herein, and a pharmacologically suitable (physiologically compatible) carrier, which may be aqueous or oil-based. In some aspects, such compositions are prepared as liquid solutions or suspensions, or as solid forms such as tablets, pills, powders and the like. Solid forms suitable for solution in, or suspension in, liquids prior to administration are also contemplated (e.g. lyophilized forms of the compounds), as are emulsified preparations. In some aspects, the liquid formulations are aqueous or oil-based suspensions or solutions. In some aspects, the active ingredients are mixed with excipients which are pharmaceutically acceptable and compatible with the active ingredients, e.g. pharmaceutically acceptable salts. Suitable excipients include, for example, water, saline, dextrose, glycerol, ethanol and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like are added. The composition of the present invention may contain any such additional ingredients so as to provide the composition in a form suitable for administration. The final amount of compound in the formulations varies but is generally from about 1-99%. Still other suitable formulations for use in the present invention are found, for example in Remington's Pharmaceutical Sciences, 22nd ed. (2012; eds. Allen, Adejarem Desselle and Felton). Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene- polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

"Pharmaceutically acceptable salts" refers to the relatively non-toxic, inorganic and organic acid addition salts, and base addition salts, of compounds of the present invention. These: salts can be prepared in situ during the final isolation and purification of the compounds. Acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorpordial herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The compositions comprising the biocomposites may be administered in vivo by any suitable route including but not limited to: inoculation or injection (e.g. intravenous, intraperitoneal, intramuscular, subcutaneous, and the like); topical application; and/or by absorption through epithelial or mucocutaneous linings (e.g., nasal, oral, vaginal, rectal, gastrointestinal mucosa, and the like). Other suitable means include but are not limited to: inhalation (e.g. as a mist or spray), orally (e.g. as a pill, capsule, liquid, etc.), incorporated into dressings or bandages (e.g. lyophilized forms may be included directly in a dressing), etc. In preferred embodiments, the mode of administration is oral or by injection.

In addition, the compositions may be administered in conjunction with other treatment modalities such as substances various chemotherapeutic agents, various antibiotic agents, and the like.

Uses of the Biocomposites

In some aspects, the biocomposites disclosed herein are used as anticoagulants ("blood thinners"). Accordingly, the biocomposites are used in methods of preventing or dissolving bloodclots in a subject in need thereof. The subjects are generally mammals, typically humans. However, veterinary applications of this technology are also encompasses.

The methods involve administering to a subject a therapeutically effective amount of a biocomposite comprising *Azadirachta indica* leaf powder crosslinked to S-CMC. Generally, the therapeutically effective amount ranges from about 0.05 to 0.3 mg/kg of body weight. Preferably, the therapeutically effective amount ranges from about 0.04 to 0.2 mg/kg of body weight.

Subjects who are treated with the biocomposites may be in need of an anticoagulant for any of a variety of reasons or to treat a variety of maladies. Many people with congenital heart defects need to take anticoagulants (blood thinners). Common reasons for this type of treatment include heart valve replacements, heart rhythm disorders or prior complicated surgeries such as the Fontan operation. Examples of diseases or conditions which are treated or prevented using the biocomposites disclosed herein include but are not limited to: various heart conditions such as myocardial infarction; disease and conditions related to atrial fibrillation, which may or may not be age-related, e.g. caused by abnormalities, defects or damage to the heart, heart attacks, an overactive thyroid gland, a metabolic imbalance, high blood pressure, lung disease, sick sinus node syndrome, viral infections, sleep apnea, pneumonia, high cholesterol, high blood pressure, diabetes and the like; they may be used after ablation therapy; to prevent or treat thromboembolic strokes, deep vein thrombosis and/or pulmonary embolism; etc.

The biocomposites may be taken prophylactically, e.g. before heart or other surgery for which anti-blooding measures are advisable, or may be taken after symptoms and diagnosis of a disease or condition requiring treatment with an anticoagulant. Further, the biocomposites may be used in conjunction with other suitable measures to treat the disease or condition, e.g. for atrial fibrillation: electrical shock or/or other medications, atrial fibrillation ablation (heat (radiofrequency energy) and/or cold (cryoablation), other anticoagulants; and the like.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Representative illustrative methods and materials are herein described;

methods and materials similar or equivalent to those described herein can also be used in the practice or testing of the present invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE

1. Abstract

Green synthesis of polymeric biocomposites using natural herb has fascinated anticoagulant activity due to its eco-friendly and non-toxic behavior towards various physical and chemical actions. Herein, we introduced a simple and eco-friendly approach for the fabrication of a newly hybrid type of biocomposite based on sulfated carboymethyl cellulose (S-CMC) and *Azadirachta Indica* leaf powder (S-CMC/NLP). Firstly, carboxymethyl cellulose was functionalized into S-CMC by reacting with $N(SO_3Na)_3$ a non-toxic sulfating agent. Three types of S-CMC/NLP biocomposites were developed by varying the concentration of NLP. The structural features of S-CMC/NLP biocomposites were characterized by FE-SEM, EDX, and XRD. FTIR confirms that S-CMC/NLP biocomposite exhibits $COO^-$, $-OH$ and $SO^{3-}$ groups, that suggesting the structural similarity to heparin. In addition, the anticoagulant effect of S-CMC/NLP biocomposite was measured by PT and APTT assays. The overall investigations of the proposed S-CMC/NLP biocomposites showed the potential as new safe and effective candidate for anticoagulant activity.

2. Experimental 2.1. Materials and Methods

Sodium carboxymethyl cellulose sodium salt (having low viscosity, viscosity of a 1% solution in water at 20 C 30-70 c/s. pH of 2% solution 6-8) was purchased from BDH Chemicals Pvt. Ltd. Poole, England. Sodium nitrite and sodium bisulfite were procured from Fisher Scientific Chemicals Pvt. Ltd. Sodium hydroxide, ethanol, and acetone were purchased from Sigma-Aldrich (USA), *Azadirachta indica* (neem) leaves were collected from Jeddah, Saudia Arabia and other reagents were of analytical grade and were utilized without additional purification.

2.2. Accumulation and Preparation of *A. Indica* Leaves (NLP) Powder

Fresh leaves of *A. indica* (neem) were collected in Jeddah, Saudia Arabia. The young fresh leaves were separated from twigs, thoroughly washed with tap water four times, treated with double distilled water (DDW) three times and then driec in a hot air oven at 40° C. for 72 h. The dried leaves were ground into fine powder using a mortar and pestle. The obtained leaf powder was washed with acetone and DDW to remove any dirt or impurities and then dried at 37° C. Finally, the dried leaf powder was composited with S-CMC at varying concentrations.

2.3. Fabrication of Sulfated-CMC and Biocomposite

The synthesis of sulfated-CMC (S-CMC) was performed partially as given in the previous literature but with modifications [36]. First, a special sulfating agent was prepared using sodium nitrite and sodium bisulfate. Typically, 0.1 M sodium bisulfate was dissolved in 80 mL DDW in a round bottom flask fitted with a condenser. 1 M sodium nitrite prepared in 20 mL DDW was carefully added dropwise into the round bottom flask at 90° C. over about a 1.5 h period with constant mechanical agitation to form $(N(SO_3Na)_3)$. The pH of prepared sulfating agent was then adjusted to ~8 using 0.2 M NaOH.

Figure 1A:
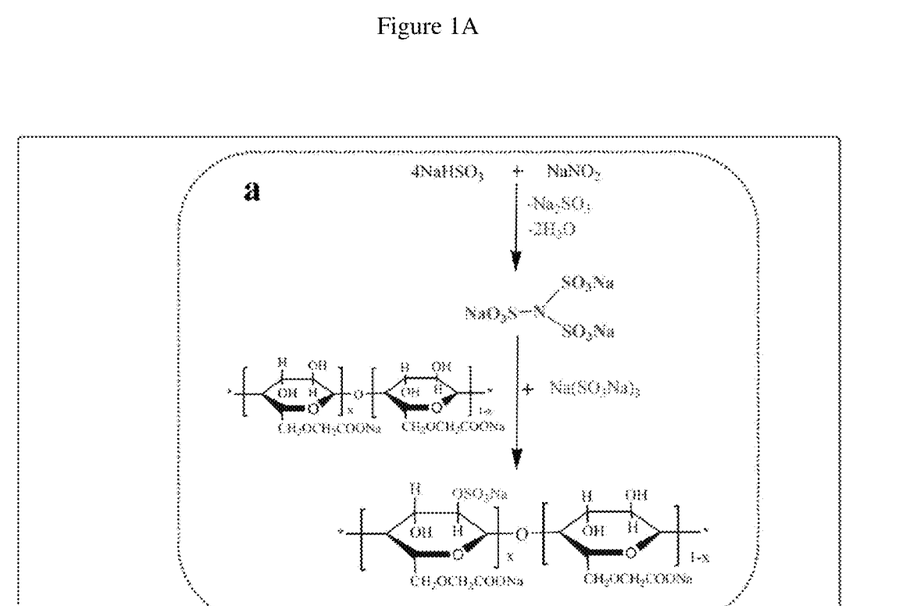
FIGS. 1A and B. (A) mechanism for the synthesis of S-CMC and (B) schematic representation of the fabrication of S-CMC/NLP bio-composites.

To form sulfated CMC, 10 g of CMC was added slowly to the solution in the round bottom flask under strong mechanical agitation (600 rpm) and the reaction was allowed to proceed for 5 h at 45° C. A highly swollen gel-suspension was formed and was then dried at 50° C. to evaporate the solvents completely. The dried S-CMC product was thoroughly washed with DDW and acetone, followed by complete drying at 60° C. (FIG. 1 (A)).

Figure 1B:
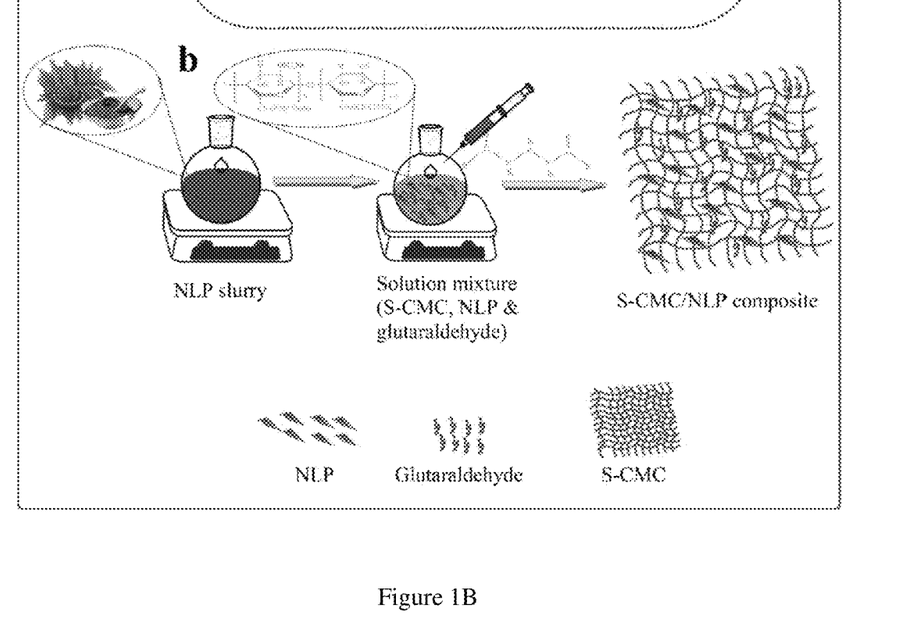

S-CMC/NLP biocomposites were fabricated using a simple solution casting method. In detail: different concentrations of *A. Indica* leaf powder (NLP) of 2.5%, 5.0% and 7.5% (w/v) were poured into 3 different round bottom flasks containing 20 mL DDW, and each flask was subjected to constant stirring for 5 h at 45° C., followed by sonication for up to 1 h. Then, 5.0% of dried S-CMC was added into all the three of the NLP solutions with constant stirring at 45° C. After adding 2 ml of gluteraldehayde into each solution, the reactions were allowed to proceed under strong mechanical agitation for 36 h at 45° C., followed by sonication for 3.5 h. Following this, the obtained S-CMC/NLP biocomposite mixtures were cast into Petri dishes and kept in a hot air oven at 60° C. up to achieve complete dryness (FIG. 1(B)). Finally, the dried S-CMC/NLP composites were treated with acetone for 2 h and then crushed into fine powder using a mortar and pestle, and samples were used for further characterizations. Herein, on the basis of varying concentration of NLP i.e., 2.5%, 5.0% and 7.5%, the synthesized S-CMC/NLP biocomposites were named as 1-S-CMC/NLP, 2-S-CMC/NLP and 3-S-CMC/NLP, respectively.

2.4. Ion Exchange Capacity and Level of Sulfation

The level of sulfation (%), which represents the average number of sulfonic ($-SO_3^-$) groups per repeating unit in the polymer backbone, can be used to investigate the ion exchange capacity (meq $g^{-1}$) of a material. The ion exchange capacity of the S-CMC was calculated through a classical titration method [37]. The level of sulfation (%) of S-CMC was carried out using a slightly modified approach as described by Unveren et al. [38,39]. Typically, ion exchange capacity is measured as $H^+$ ions are released by neutral salts and move through the polymer backbone. In brief, the dried S-CMC (0.25 g) was immersed in an aqueous solution of 1 M $HNO_3$ for 24 h, to convert the material into an $H^+$ form. Then the $H^+$-S-CMC was washed with DDW till neutralization followed by complete drying at 60° C. After that, the dried S-CMC was packed into a glass column and 1 M $NaNO_3$ at a flow rate of 0.4 ml $min^{-1}$ was used to elute the protons totally from the column. Then the exchanged protons ($H^+$) of the solution were titrated using phenolphthalein as an indicator, with (0.1 M) NaOH serving as a standard. The ion exchange capacity and level of sulfation (%) of the S-CMC was determined via the following equations:

$$IEC = \frac{\text{Concentration of NaOH} \times \text{Vol of NaOH}}{\text{Weight of dry polymer}} \quad (1)$$

$$\text{Level of sulfation}(\%) = \frac{MW_{CMC} \times IEC \times 100}{1000 - (MW_{S-CMC} - MW_{CMC}) \times IEC} \quad (2)$$

where, $MW_{CMC}$ and $MW_{S-CMC}$ are the molecular weights of the monomer units of CMC (468.176) and S-CMC (570.233), respectively.

2.5. Characterization

The elemental composition of S-CMC/NLP biocomposites was measured by energy dispersive X-ray (EDX) (Oxford instruments INCA-x-act, S. No. 56756, UK). Structural description and morphological appearance were examined by field emission scanning electron microscopy (FE-SEM) (Zeiss EVO® 50 XVP, UK). The structural pattern of the biocomposites was determined by X-ray diffraction (XRD) pattern (Rigaku, Miniflex-II-Japan) with Cu Kα at 40 kV, 40 mA, and 2q with a scan angle: 10°-80°. Chemical structures were characterized with Fourier transform infrared spectrometry (PerkinElmer 100 FT-IR Spectrometer-USA) by recording in the range of 500 to 4000 $cm^{-1}$. All the S-CMC/NLP samples were completely dried at 45° C. and packed in airtight culture tubes prior to characterizations. The anticoagulant properties of S-CMC/NLP biocomposites were recorded by PT and APTT assays.

3. Results and Discussion

The present work describes investigations of the anticoagulation properties of NLP supplemented S-CMC based biocomposites. For this, a simple and facile route was adopted to fabricate "green", cost effective and eco-friendly S-CMC/NLP biocomposites. Herein, the synthesized S-CMC/NLP biocomposites were named 1-S-CMC/NLP, 2-S-CMC/NLP and 3-S-CMC/NLP. The anticoagulant properties of polysaccharides are influenced and/or determined by structure, and the presence of sulfonated groups [40]. Therefore, the modification of CMC into S-CMC was carried out to introduce sulfonic groups into the polymer backbone. To replace traditional methods, a new-type of low cost, non-toxic, sulfating agent ($N(SO_3Na)_3$) was used to obtain S-CMC and to permit the entire sulfate modification reaction to be carried out in aqueous solution. The ion exchange capacity value of the S-CMC polysaccharide was found to be 0.25 meq/$g^{-1}$. From the experimental value of ion exchange capacity, the level of sulfation (%) of the modified polysaccharide (S-CMC) was calculated to be 12.01%.

NLP comprises active compounds that have antibacterial, antifungal and antiviral properties and is considered to be a promising natural herb owing to its probable broad spectrum therapeutic and prophylactic role due to the presence of bioactive compounds [41-45]. These bioactive compounds may also be able to alter the serum biochemical and hematological parameters of animals Furthermore, continuing with the favorable effects of A. Indica, it has been shown to have anti-oxidative and anti-inflammatory activity, cancer preventive potential, to be hepato-protective, and to be effective as an anti-diabetic agent [46-51]. The plausible interactions between S-CMC and NLP during the synthetic process may involve hydrogen bonding among H atoms of NLP (from amino and hydroxyl groups) and sulfonic groups of S-CMC. The formation of hydrogen bonds was confirmed by the shifting of the —O—H stretching wavenumber from ~3400 to 3350 $cm^{-1}$. Moreover, the fabricated S-CMC/NLP biocomposite possesses anticoagulant properties, likely due to a large profusion of hydroxyl (—OH), sulfonyl ($-SO^{3-}$) and carboxylate ($-COO^-$) functional groups on the S-CMC chain, which helps the polymer to interact with specific proteins, especially antithrombin, in a manner similar to heparin [52,53]. Finally, for the prepared S-CMC/NLP biocomposite, the experimental outcomes indicated that the modification of CMC followed by compositing with NLP enhanced its anticoagulant activity, which may helpful to promote the process of wound healing.

3.1. FT-IR Analyses

Figure 2:
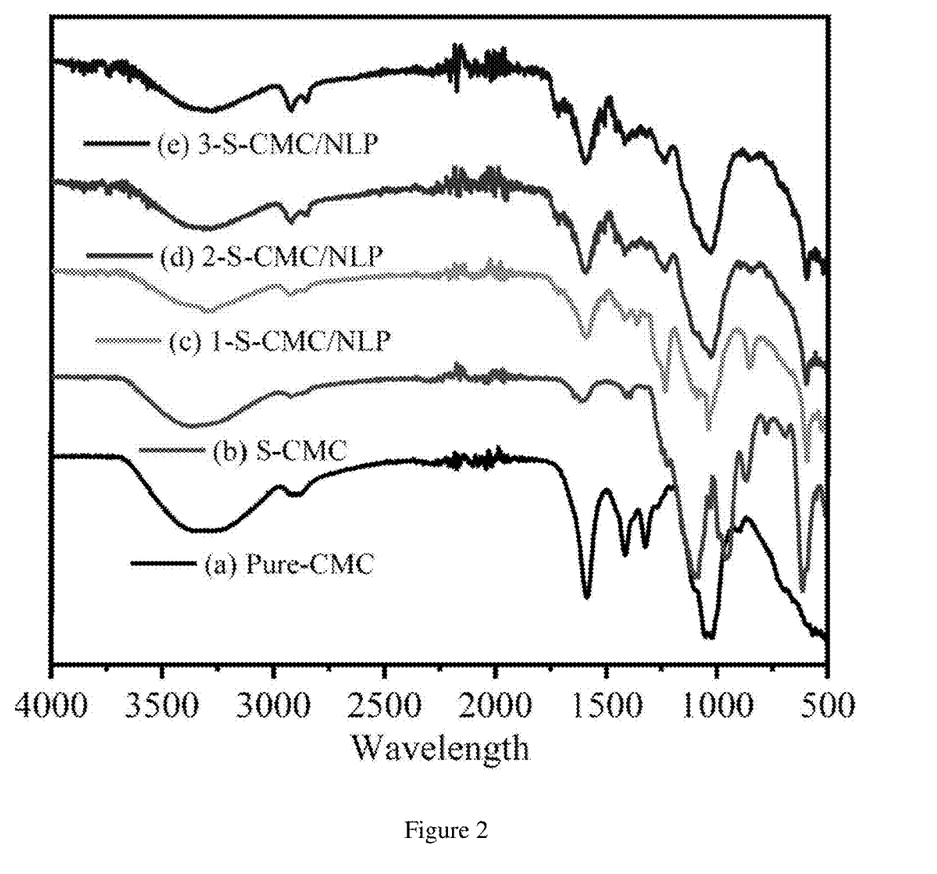
FIG. 2. FTIR spectra of (a) pure CMC, (b) S-CMC, (c) 1-S-CMC/NLP, (d) 2-S-CMC/NLP and (e) 3-S-CMC/NLP bio-composites.

The FT-IR spectra of pure CMC, S-CMC and 1-S-CMC/NLP, 2-S-CMC/NLP and 3-S-CMC/NLP biocomposites are shown in FIG. 2. Typical absorption bands of the biocomposites at ~3400, 2910, 1610, 1426 and 1054 $cm^{-1}$ were clear for all five samples. These characteristic absorption bands correspond to the —O—H, —C—H, —C═O and carbonyl-C—O stretching vibrations of CMC, S-CMC and S-CMC/NLP biocomposites, respectively [54]. Moreover, it can be observed from FIG. 2 (B) that S-CMC exhibitstwo characteristic absorption bands, one at 1229 $cm^{-1}$, ascribed to the asymmetrical stretching vibration of —S═O, and the other absorption band at 865 $cm^{-1}$, attributed to the symmetrical stretching vibration of C—O—S associated to C—O—$SO_3$ groups [55]. However, these two characteristic absorption bands were absent in the FTIR spectrum of pure CMC (FIG. 2 (A)), which shows that the sulfation of CMC was successfully achieved by introducing sulfate groups into the polymer chain of S-CMC. On the other hand, due to hydrogen bonding interactions of NLP (e.g. from amino and hydroxyl groups) and sulfonyl group of S-CMC, absorption bands due to —O—H stretching shift from ~3400 to 3350 cm$^{-1}$ (FIG. 2 (C-E)). It is noted that the intensity of characteristic absorption bands assigned to —OSO$_3$ groups in S-CMC diminished in 1-, 2- and 3-S-CMC/NLP biocomposites with marginal shifts from 870 cm$^{-1}$ to 854 (FIG. 2 (C-E)), which agrees with and confirms successful interactions among the active sites present within the biocomposites.

3.2. FE-SEM Analysis

Figure 3A:
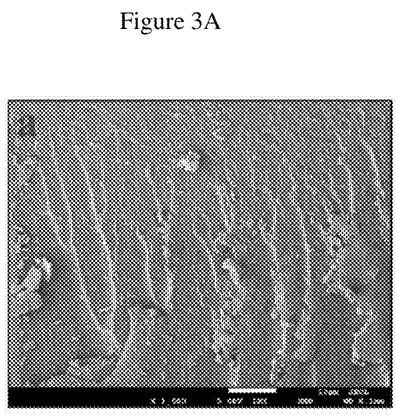
FIG. 3A-D. FE-SEM images of S-CMC/NLP bio-composite (A, B) SEM image of pure S-CMC, and C, D) SEM images of S-CMC supplemented NLP based bio-composite scanned at different magnifications.
Figure 3B:
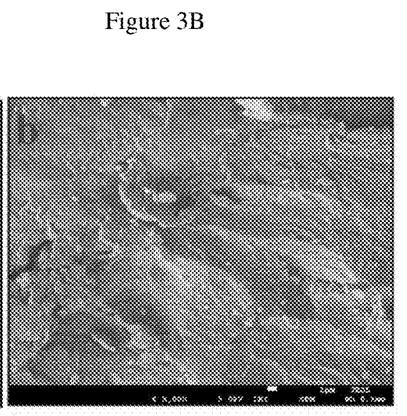
Figure 3C:
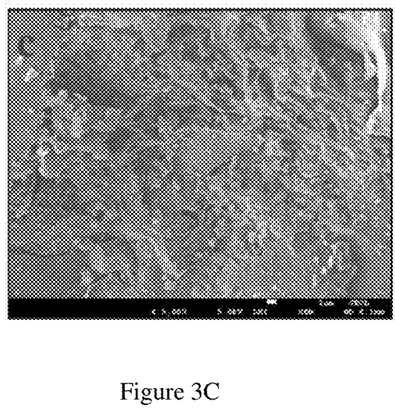
Figure 3D:
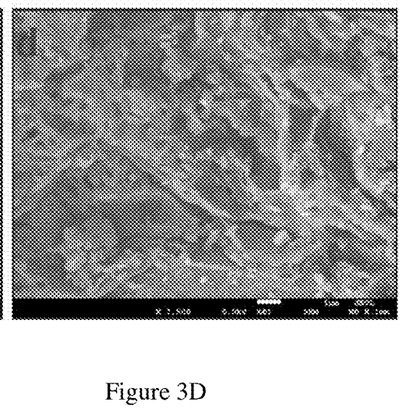

FE-SEM micrographs were taken to observe the shape and surface morphology of the S-CMC/NLP biocomposites. FIG. 3D shows FE-SEM images of pure S-CMC and S-CMC/NLP biocomposites at low (left) and high magnification (right). The surface of the pure S-CMC biomaterial has compact, homogeneous structural integrity with low roughness on the surface (FIG. 3 (A,B)). The morphology of S-CMC alone is relatively more rigid (FIG. 3 (A,B), which could be due to more intensive attraction among the polymer backbones after sulfation. On the other hand, by compositing S-CMC with NLP, which increases NLP and reduces S-CMC amounts, the whole surface becomes more porous, rougher and hilly (FIG. 3 (C,D)). In addition, spherical and differently shaped aggregates were observed on the surface of the S-CMC/NLP biocomposites (FIG. 3C). Further magnification (FIG. 3D) suggests the presence of granular aggregates strongly bound, engulfed and uniformly dispersed on the surface of the biocomposite as a "wall-forming" material. These observations confirm that the biocomposites have a well-defined matrix.

3.3. EDX Analysis

EDX analysis was carried out to confirm the sulfonation of CMC and the composition of the S-CMC/NLP based biocomposites (FIG. 4). For the pure S-CMC biomaterial (FIG. 4 (A,B)), the presence of sharp elemental peaks of S along C, O and Na confirm the sulfonation of the CMC biopolymer. The presence of S can also be observed in the composition of both pure S-CMC and S-CMC/NLP, which suggests the successful modification of sodium CMC to S-CMC (FIG. 4 (B and D)). Furthermore, in the composition of S-CMC/NLP, the additional elemental peaks of K and Cl along with C, O, S and Na can be clearly observed (FIG. 4 (D)). Other elemental peaks observed in both EDX spectra were due to the presence of various functional groups in the S-CMC chain.

3.4. XRD Analysis

Figure 4A:
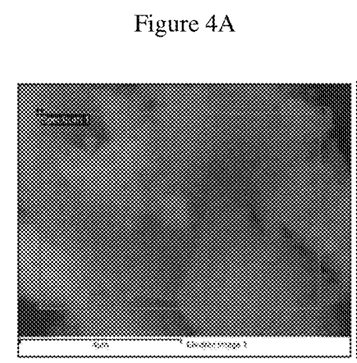
FIG. 4A-D. EDAX analysis of (A, B) S-CMC and (C, D) S-CMC/NLP bio-composite fabricated through green chemical approach.
Figure 4B:
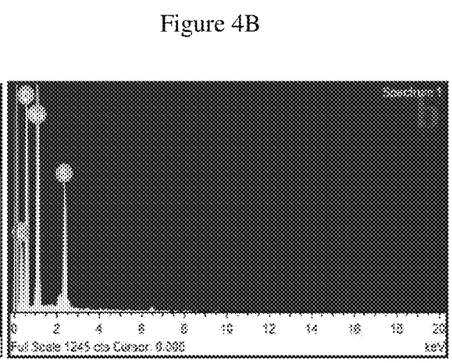
Figure 4C:
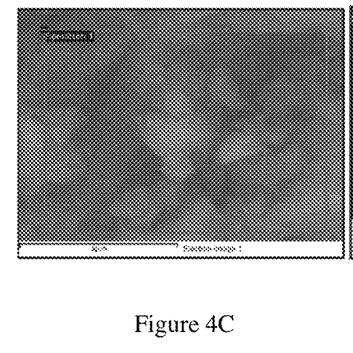
Figure 4D:
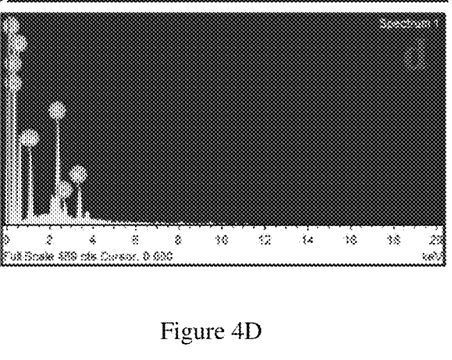
Figure 5:
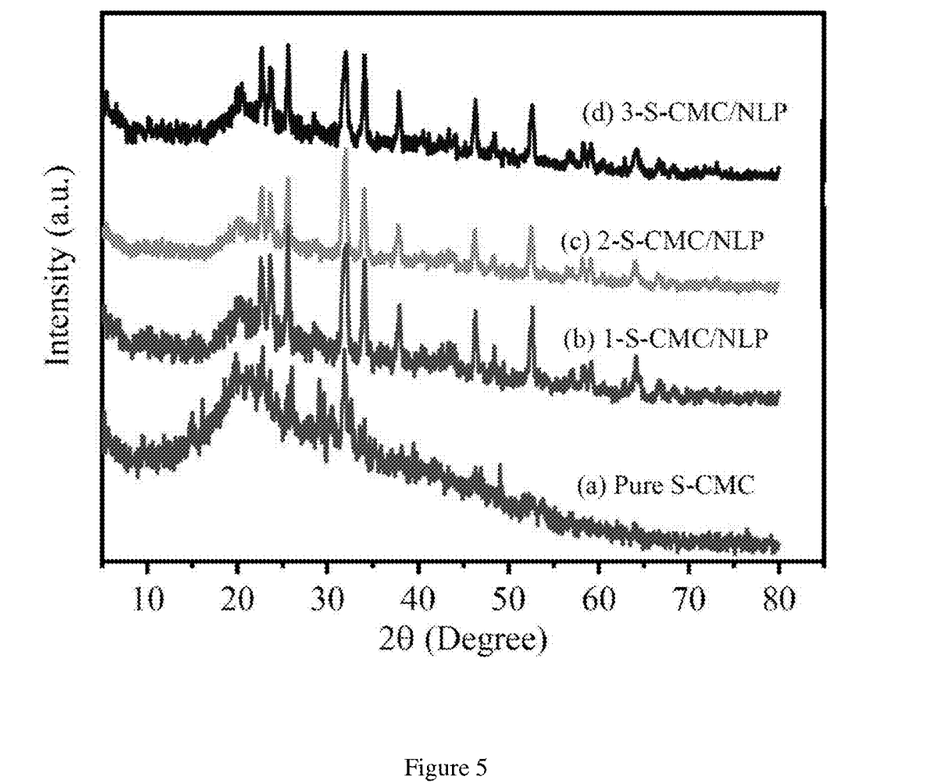
FIG. 5. XRD diffraction patterns of (a) S-CMC, (b) 1-S-CMC/NLP, (c) 2-S-CMC/NLP and (d) 3-S-CMC/NLP bio-composites.

The XRD pattern of S-CMC, the 1-, 2- and 3-S-CMC/NLP biocomposites is shown in FIG. 5. It can be observed from FIG. 5 (A) that sulfated-CMC represents typically non-crystalline morphology, and the wide diffraction peak in the region of 2θ=20-23° can be attributed to the reflection of the (200) plane, confirming the amorphous nature (FIG. 5 (A)) [56]. This similar broad peak (2θ=20-23°)can also be seen in the XRD pattern of the 1-, 2- and 3-S-CMC/NLP biocomposites (FIG. 5 (B-D)), which indicates successful composition of NLP with S-CMC without impairing the nature of modified S-CMC. However, after modification of S-CMC with NLP, the intensity of the diffraction peaks increases due to the presence of different metal elements in NLP (FIG. 4 C, D). Therefore, the XRD pattern of the synthesized biocomposites exhibits small peaks of 2θ values (FIG. 5 (B-D)). The increased intensity of diffraction peaks together with the presence of broad diffraction peaks) (2θ=20-23°) indicates an amorphous nature with a semi-crystalline structure of the fabricated S-CMC/NLP based biocomposites.

3.5. Anticoagulant Activity of S-CMC/NLP Based Biocomposite

Figure 6A:
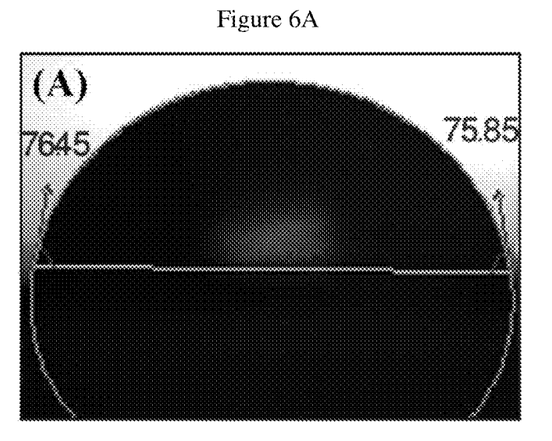
FIGS. 6A and B. (A) Image of contact angle in the form of a water droplet for S-CMC/NLP biocomposite. (B) Coagulation time in seconds (APTT and PT) levels for control compared to the fabricated S-CMC/NLP bio-composite (PT(s) and APTT(s) represent biocomposite SCMC/NLP).
Figure 6B:
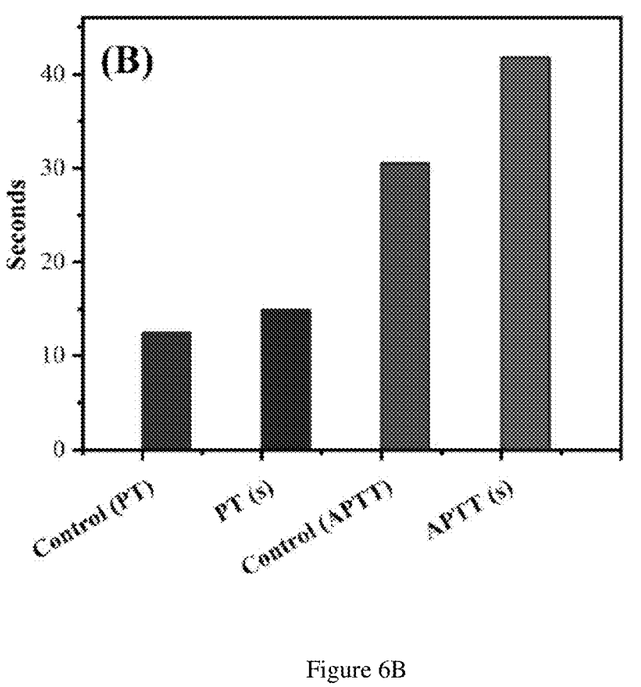

The hydrophilicity of biomaterials has affirmative impacts on anticoagulant activities and contact angle measurements are an important parameter to investigate hydrophilicity. Contact angle determination can be achieved by assessment of a water droplet on the surface of a biocomposite material. A low contact angle value indicates high hydrophilicity. As shown in FIG. 6 (A), S-CMC/NLP based biocomposites showed a value of 76.45° (left)/75.85° (right). This low contact angle value confirms the hydrophilic nature of the S-CMC/NLP biocomposites. A suitably hydrophilic composite surface can suppress adhesion of platelets to a composite material, and is essential for blood compatibility [57]. Platelets are negative charged because of the occurrence of a negatively charged sugar (sialic acid) on their surfaces [58]. The negatively charged sulfonyl (—SO$^{3-}$) and carboxylate (—COO$^-$) groups of S-CMC/NLP-based biocomposites are electro-statically repellant toward platelets, which hinders the absorption of platelets onto the S-CMC/NLP surface [57]. Thus, the hydrophilic nature of S-CMC/NLP biocomposites due to (—SO$^{3-}$) and carboxylate (—COO$^-$) groups obstructs platelets adhesion on the material surface, further establishing robust anticoagulant activities of the biocomposites. Low platelet adhesion and activation demonstrates enhanced blood compatibility. The activation of blood plasma proteins induces blood clotting at the time of their adsorption on an external surface. The activation of coagulation factors causes transformation of prothrombin into thrombin, which induces the transformation of fibrinogen into fibrin protein and produces a blood clot [59]. There are two main routes to activate plasma proteins and induce blood coagulation: (1) the extrinsic pathway and the intrinsic pathway [60]. Therefore, the time required for blood clotting is considered to be a critical factor when appraising any external surface in order to establish its antithrombogenicity. Partial thromboplastin time (PT) and activated partial thromboplastin time (APTT) are two measures used to elucidate the clotting variations that are concerned with extrinsic and intrinsic pathways and also are considered as good indicators to determine the clotting time [61]. FIG. 6 (B) shows the anticoagulant activity of the fabricated S-CMC/NLP-based biocomposite compared to the control PT and APTT values. The coagulation factors measured by the APTT assay follow the intrinsic pathway, while after the addition of a plasma sample, the PT assay indicates the formation time of fibrin from fibrinogen [62]. As can be observed in FIG. 6 (B), PT and APTT values for the 2-S-CMC/NLP biocomposite were prolonged in comparison with control values (pure plasma). This indicates that the biocomposite possesses high PT and APTT levels in comparison controls, and that the integration of NLP with S-CMC results in improved anticoagulant activities.

The investigation of the intrinsic pathway of coagulation system through the APTT evaluation confirmed that the 2-NLP/S-CMC biocomposite dose-dependently (0.045-0.28 mg/mL) prolonged the time of blood coagulation compared to the control (pure plasma). Increasing concentrations of the biocomposites (1-S-CMC/NLP, 2-S-CMC/NLP and 3-S-CMC/NLP) resulted in increases in coagulation time. Furthermore, the 2-NLP/S-CMC biocomposite increased the coagulation time at 0.28 mg/mL, being better than the 1-NLP/S-CMC and 3-NLP/S-CMC) biocomposites. However, the effect was much less than that of heparin; a larger amount of 2-NLP/S-CMC biocomposite was needed in order to attain anticoagulant activity similar to that of heparin.

The anti-inflammatory activity of NLP is due to presence of the bioactive compound limonoid [63,64]. Limonoid is a furanolactone, recognized for its inhibitory effects on the production of inflammatory mediators, and is also considered as a pain anesthetizer, as it promotes the activation of endogenous opioid pathways [20,21,64]. However, such herbs have limited usefulness in their natural forms. These limitations have been overcome by formulating the new biocomposites described herein, e.g. to serve as an effective anti-coagulant material. Furthermore, polyanionic S-CMC can interact with cationic groups present on the cell surface thereby causing enhanced membrane permeability, which in turn leads to leakage and disruption of cellular proteins. This electrostatic interaction facilitates the high activity of S-CMC against different gram negative and gram-positive bacteria, and can be further enhanced by adding A. indica extract (NLP) [65,66]. On the other hand, the high degree of sulfation could enhance the density of negativity to inhibit the activity of thrombin IIa factor and Xa factor [67]. Therefore, the sulfated form of CMC inhibits thrombin Xa factor and IIa factor to produce the anticoagulant activity. APTT assay is an essential indicator of coagulation activity. The APTT value suggested that the anticoagulant activity of S-CMC/NLP based biocomposites was good. Therefore, it can be concluded that sulfate groups play a significant role in enhancing anticoagulant activity. Similar to heparin, S-CMC/NLP based biocomposites with negatively charge sulfate groups neutralize the positively charged residues of amino acids present in anti-thrombin in order to enhance anticoagulant activities. From this analysis, we speculated that, like the heparin polymer, the S-CMC/NLP biocomposites possess anticoagulant activities due to a large profusion of hydroxyl (—OH), sulfonyl (—$SO^{3-}$) and carboxylate (—$COO^-$) functional groups on the S-CMC chain, which facilitate the biocomposite's interactions with the active site of specific proteins, especially antithrombin, [52,53]. The negatively charged sulfonyl (—$SO^{3-}$) and carboxylate (—$COO^-$) groups reduce the proteins adsorption through the electrostatic effect, which inhibits the activation of the intrinsic cascade [68]. This negatively charged surface is accessible for binding coagulation factors, which results in long APTTs [69]. As the coagulation cascade is initiated, activation and aggregation of platelets induces thrombosis and subsequent coagulation [70]. Therefore, the present research has shown that the combination of NLP of A. indica and S-CMC synergistically into the biocomposites described herein stimulates anticoagulant activity through causing an improved inflammatory response by interacting with the active site of specific proteins. Moreover, S-CMC and NLP both are biodegradable and nontoxic towards mammalian cells.

4. Conclusion

In the current work, a cost effective and biocompatible biocomposite was successfully prepared from sulfated-CMC and NLP (S-CMC/NLP) through a simple and easy approach in aqueous medium without using any toxic reagents. The modification of CMC was carried out in aqueous medium using a neutral N($SO_3$Na)$_3$ sulfating agent. After that, S-CMC was composited with NLP to obtain the biocomposites. The composition and structure of the biocomposites were characterized by FT-IR, FE-SEM, EDX and XRD studies. FT-IR analysis showed the characteristic absorption bands of at 1229 and 865 $cm^{-1}$ assigned to sulfate ester bonds, which confirms the introduction of sulfate groups. The interactions between S-CMC and NLP caused by hydrogen bonding was confirmed by the shifting of the —O—H stretching wavenumber from ~3400 to 3350 cm−1. The XRD pattern showed that S-CMC/NLP corresponded to a semi-crystalline structure without impairing the nature of the S-CMC. The anticoagulant properties of the S-CMC/NLP biocomposites were measured by PT and APTT assays. The results revealed that the biocomposites exhibited high anticoagulant activity. According to the Pt and APTT experiments, the S-CMC/NLP exhibited an effective anticoagulant effect owing to the coexistence of —$COO^-$, —$SO^{3-}$, and —OH on the surface of the biocomposites.

ACKNOWLEDGEMENTS

The authors are grateful to the Department of Chemistry, King Abdulaziz University, Saudi Arabia for providing research facilities and granting the permission to publish this work. This work was supported by the Ministry of Education, King Abdulaziz University Administration of Support for Research and Development Initiatives, Kingdom of Saudi Arabia, under the research scheme Post-Doctoral Researcher awarded to Dr Ajahar Khan.

REFERENCES

[1] A. J. T. Teo, A. Mishra, I. Park, Y.-J. Kim, W.-T. Park, Y.-J. Yoon, Polymeric Biomaterials for Medical Implants and Devices, ACS Biomater. Sci. Eng. 2 (2016) 454-472. doi:10.1021/acsbiomaterials.5b00429.

[2] N. Weber, H. P. Wendel, G. Ziemer, Hemocompatibility of heparin-coated surfaces and the role of selective plasma protein adsorption, Biomaterials. 23 (2002) 429-439. doi:10.1016/S0142-9612(01)00122-3.

[3] A. Bentolila, I. Vlodaysky, C. Haloun, A. J. Domb, Synthesis and heparin-like biological activity of amino acid-based polymers, Polym. Adv. Technol. 11 (2000) 377-387. doi:10.1002/1099-1581(200008/12)11:8/12<377::AID-PAT985>3.0.CO;2-D.

[4] Y. Tamada, M. Murata, T. Hayashi, K. Goto, Anticoagulant mechanism of sulfonated polyisoprenes, Biomaterials. 23 (2002) 1375-1382. doi:10.1016/S0142-9612(01)00258-7.

[5] G. Rollason, M. V. Sefton, Inactivation of thrombin in heparin-PVA coated tubes, J. Biomater. Sci. Polym. Ed. 1 (1989) 31-41. doi:10.1163/156856289X00046.

[6] J. PARK, M. ACAR, A. AKTHAKUL, W. KUHLMAN, A. MANES, Polysulfone-poly(ethylene glycol) graft copolymers for surface modification of polysulfone membranes, Biomaterials. 27 (2006) 856-865. doi:10.1016/j.biomaterials.2005.07.010.

[7] Y. BYUN, H. A. JACOBS, S. W. KIM, Binding Kinetics of Thrombin and Antithrombin III with Immobilized Heparin Using a Spacer, ASAIO J. 38 (1992) M649-M653. doi:10.1097/00002480-199207000-00117.

[8] J. Weitz, New Anticoagulant Strategies, Drugs. 48 (1994) 485-497. doi:10.2165/00003495-199448040-00001.

[9] M. Rusnati, P. Oreste, G. Zoppetti, M. Presta, Biotechnological Engineering of Heparin/Heparan Sulphate: A Novel Area of Multi-Target Drug Discovery, Curr. Pharm. Des. 11 (2005) 2489-2499. doi:10.2174/1381612054367553.

[10] P. Vongchan, W. Sajomsang, D. Subyen, P. Kongtawelert, Anticoagulant activity of a sulfated chitosan, Carbohydr. Res. 337 (2002) 1239-1242. doi:10.1016/S0008-6215(02)00098-8.

[11] L. Fan, L. Jiang, Y. Xu, Y. Zhou, Y. Shen, W. Xie, Z. Long, J. Zhou, Synthesis and anticoagulant activity of sodium alginate sulfates, Carbohydr. Polym. 83 (2011) 1797-1803. doi:10.1016/j.carbpol.2010.10.038.

[12] K. Zhang, D. Peschel, E. Brendler, T. Groth, S. Fischer, Synthesis and Bioactivity of Cellulose Derivatives, Macromol. Symp. 280 (2009) 28-35. doi:10.1002/masy.200950604.

[13] N. Aarne, E. Kontturi, J. Laine, Carboxymethyl cellulose on a fiber substrate: the interactions with cationic polyelectrolytes, Cellulose. 19 (2012) 2217-2231. doi:10.1007/s10570-012-9793-2.

[14] D. R. Biswal, R. P. Singh, Characterisation of carboxymethyl cellulose and polyacrylamide graft copolymer, Carbohydr. Polym. 57 (2004) 379-387. doi:10.1016/j.carbpol.2004.04.020.

[15] P. N. Bhandari, D. D. Jones, M. A. Hanna, Carboxymethylation of cellulose using reactive extrusion, Carbohydr. Polym. 87 (2012) 2246-2254. doi:10.1016/j.carbpol.2011.10.056.

[16] M. Černík, V. V. Thekkae Padil, Green synthesis of copper oxide nanoparticles using gum karaya as a biotemplate and their antibacterial application, Int. J. Nanomedicine. (2013) 889. doi:10.2147/IJN.S40599.

[17] N. P. S. Acharyulu, P. Madhu Kiran, P. Kollu, R. L. Kalyani, S. V. N. Pammi, Room temperature synthesis and evaluation of antibacterial activity of silver nanoparticles using Phyllanthus amarus leaf extract, J. Bionanoscience. 8 (2014) 190-194. doi:10.1166/jbns.2014.1220.

[18] K. Rajendaran, R. Muthuramalingam, S. Ayyadurai, Green synthesis of Ag—Mo/CuO nanoparticles using Azadirachta indica leaf extracts to study its solar photocatalytic and antimicrobial activities, Mater. Sci. Semicond. Process. 91 (2019) 230-238. doi:10.1016/j.mssp.2018.11.021.

[19] R. R. Chattopadhyay, Effect of Azadirachta indica hydroalcoholic leaf extract on the cardiovascular system, Gen. Pharmacol. Vasc. Syst. 28 (1997) 449-451. doi:10.1016/S0306-3623(96)00184-X.

[20] M. Schumacher, C. Cerella, S. Reuter, M. Dicato, M. Diederich, Anti-inflammatory, pro-apoptotic, and antiproliferative effects of a methanolic neem (Azadirachta indica) leaf extract are mediated via modulation of the nuclear factor-κB pathway, Genes Nutr. 6 (2011) 149-160. doi:10.1007/s12263-010-0194-6.

[21] M. Naik, D. Agrawal, R. Behera, A. Bhattacharya, S. Dehury, S. Kumar, Study of anti-inflammatory effect of neem seed oil (Azadirachta indica) on infected albino rats, J. Heal. Res. Rev. 1 (2014) 66. doi:10.4103/2394-2010.153880.

[22] E. Hernández-Aquino, P. Muriel, Beneficial effects of naringenin in liver diseases: Molecular mechanisms, World J. Gastroenterol. 24 (2018) 1679-1707. doi:10.3748/wjg.v24.i16.1679.

[23] F. L. A. Batista, L. M. G. Lima, I. A. Abrante, J. I. F. de Araújo, F. L. A. Batista, I. A. Abrante, E. A. Magalhães, D. R. de Lima, M. da C. L. Lima, B. S. do Prado, L. F. W. G. Moura, M. I. F. Guedes, M. K. A. Ferreira, J. E. S. A. de Menezes, S. A. A. R. Santos, F. R. S. Mendes, R. A. Moreira, A. C. O. Monteiro-Moreira, A. R. Campos, F. E. A. Magalhães, Antinociceptive activity of ethanolic extract of Azadirachta indica A. Juss (Neem, Meliaceae) fruit through opioid, glutamatergic and acid-sensitive ion pathways in adult zebrafish (Danio rerio), Biomed. Pharmacother. 108 (2018) 408-416. doi:10.1016/j.biopha.2018.08.160.

[24] A. Roma, P. Ovadje, M. Steckle, L. Nicoletti, A. Saleem, S. Pandey, Selective Induction of Apoptosis by Azadarichta indica Leaf Extract by Targeting Oxidative Vulnerabilities in Human Cancer Cells, J. Pharm. Pharm. Sci. 18 (2015) 729. doi:10.18433/J3VG76.

[25] S. Saleem, G. Muhammad, M. A. Hussain, S. N. A. Bukhari, A comprehensive review of phytochemical profile, bioactives for pharmaceuticals, and pharmacological attributes of Azadirachta indica, Phyther. Res. 32 (2018) 1241-1272. doi:10.1002/ptr.6076.

[26] P. Kundu, S. Barik, K. Sarkar, A. Bose, R. Baral, S. Laskar, Chemical investigation of neem leaf glycoprotein used as immunoprophylactic agent for tumor growth restriction, Int. J. Pharm. Pharm. Sci. 7 (2015) 195-199.

[27] A. Dayakar, S. Chandrasekaran, J. Veronica, S. Sundar, R. Maurya, In vitro and in vivo evaluation of antileishmanial and immunomodulatory activity of Neem leaf extract in Leishmania donovani infection, Exp. Parasitol. 153 (2015) 45-54. doi:10.1016/j.exppara.2015.02.011.

[28] S. Banerjee, T. Ghosh, S. Barik, A. Das, S. Ghosh, A. Bhuniya, A. Bose, R. Baral, Neem Leaf Glycoprotein Prophylaxis Transduces Immune Dependent Stop Signal for Tumor Angiogenic Switch within Tumor Microenvironment, PLoS One. 9 (2014) e110040. doi:10.1371/journal.pone.0110040.

[29] F. R. Durrani, N. Chand, M. Jan, A. Sultan, Z. Durrani, S. Akhtar, Immunomodulatory and growth Promoting Effects of Neem Leaves Infusion in Broiler Chicks, Sarhad J. Agric. 24 (2008) 655-659. http://www.aup.edu.pk/sj_pdf/IMMUNOMODULATORY AND GROWTH PROMOTING.pdf.

[30] S. Priyanka Dash, S. Dixit, S. Sahoo, Phytochemical and Biochemical Characterizations from Leaf Extracts from Azadirachta Indica: An Important Medicinal Plant, Biochem. Anal. Biochem. 06 (2017). doi:10.4172/2161-1009.1000323.

[31] T. O. Omóbòwálé, A. A. Oyagbemi, O. A. Adejumobi, E. V. Orherhe, A. S. Amid, A. A. Adedapo, H. O. Nottidge, M. A. Yakubu, Preconditioning with Azadirachta indica ameliorates cardiorenal dysfunction through reduction in oxidative stress and extracellular signal regulated protein kinase signalling, J. Ayurveda Integr. Med. 7 (2016) 209-217. doi:10.1016/j.jaim.2016.08.006.

[32] A. Arumugam, P. Agullo, T. Boopalan, S. Nandy, R. Lopez, C. Gutierrez, M. Narayan, L. Rajkumar, Neem leaf extract inhibits mammary carcinogenesis by altering cell proliferation, apoptosis, and angiogenesis, Cancer Biol. Ther. 15 (2014) 26-34. doi:10.4161/cbt.26604.

[33] J. Bajdik, Z. Makai, O. Berkesi, K. Süvegh, T. Marek, I. Erős, K. Pintye-Hódi, Study of the effect of lactose on the structure of sodium alginate films, Carbohydr. Polym. 77 (2009) 530-535. doi:10.1016/j.carbpol.2009.01.022.

[34] M. A. Alzohairy, Therapeutics Role of Azadirachta indica (Neem) and Their Active Constituents in Diseases Prevention and Treatment, Evidence-Based Complement. Altern. Med. 2016 (2016) 1-11. doi:10.1155/2016/7382506.

[35] M. Kiranmai, C. B. Mahender Kumar, M. D. Ibrahim, Free radical scavenging activity of neem tree (Azadirachta indica A. Juss var., Meliaceae) root bark extract, Asian J. Pharm. Clin. Res. 4 (2011) 134-136.

[36] L. Fan, X. Zhou, P. Wu, W. Xie, H. Zheng, W. Tan, S. Liu, Q. Li, Preparation of carboxymethyl cellulose sulfates and its application as anticoagulant and wound dressing, Int. J. Biol. Macromol. 66 (2014) 245-253. doi:10.1016/j.ijbiomac.2014.02.040.

[37] Inamuddin, A. Khan, M. Luqman, A. Dutta, Kraton based ionic polymer metal composite (IPMC) actuator, Sensors Actuators A Phys. 216 (2014) 295-300. doi:http://dx.doi.org/10.1016/j.sna.2014.04.015.

[38] E. E. Unveren, T. Erdogan, S. S. Çelebi, T. Y. Inan, Role of post-sulfonation of poly(ether ether sulfone) in proton conductivity and chemical stability of its proton exchange membranes for fuel cell, Int. J. Hydrogen Energy. 35 (2010) 3736-3744. doi:10.1016/j.ijhydene.2010.01.041.

[39] E. E. Unveren, T. Y. Inan, S. S. Çelebi, Partially Sulfonated Poly(1,4-phenylene ether-ether-sulfone) and Poly(vinylidene fluoride) Blend Membranes for Fuel Cells, Fuel Cells. (2013) n/a-n/a. doi:10.1002/fuce.201300075.

[40] T. Maruyama, T. Toida, T. Imanari, G. Yu, R. J. Linhardt, Conformational changes and anticoagulant activity of chondroitin sulfate following its O-sulfonation, Carbohydr. Res. 306 (1998) 35-43. doi:10.1016/S0008-6215(97)10060-X.

[41] K. Biswas, I. Chattopadhyay, R. K. Banerjee, U. Bandyopadhyay, Biological activities and medicinal properties of neem (Azadirachta indica), Curr. Sci. 82 (2002) 1336-1345.

[42] N. Alzoreky, K. Nakahara, Antibacterial activity of extracts from some edible plants commonly consumed in Asia, Int. J. Food Microbiol. 80 (2003) 223-230. doi:10.1016/S0168-1605(02)00169-1.

[43] A. Vanka, S. Tandon, S. R. Rao, N. Udupa, P. Ramkumar, The effect of indigenous Neem Azadirachta indica [correction of (Adirachta indica)] mouth wash on *Streptococcus mutans* and lactobacilli growth, Indian J. Dent. Res. 12 (2001) 133-144. http://europepmc.org/abstract/MED/11808064.

[44] W. Fabry, P. Okemo, R. Ansorg, Fungistatic and fungicidal activity of East African medicinal plants, Mycoses. 39 (1996) 67-70. doi:10.1111/j.1439-0507.1996.tb00087.x.

[45] M. Parida, C. Upadhyay, G. Pandya, A. Jana, Inhibitory potential of neem (Azadirachta indica Juss) leaves on Dengue virus type-2 replication, J. Ethnopharmacol. 79 (2002) 273-278. doi:10.1016/S0378-8741(01)00395-6.

[46] S. N. Upadhyay, S. Dhawan, S. Garg, G. P. Talwar, Immunomodulatory effects of neem (Azadirachta indica) oil, Int. J. Immunopharmacol. 14 (1992) 1187-1193. doi:10.1016/0192-0561(92)90054-O.

[47] S. Arivazhagan, B. Velmurugan, V. Bhuvaneswari, S. Nagini, Effects of Aqueous Extracts of Garlic (Allium sativum) and Neem (Azadirachta indica) Leaf on Hepatic and Blood Oxidant-Antioxidant Status During Experimental Gastric Carcinogenesis, J. Med. Food. 7 (2004) 334-339. doi:10.1089/jmf.2004.7.334.

[48] R. R. Chattopadhyay, Possible mechanism of hepatoprotective activity of Azadirachta indica leaf extract: Part II, J. Ethnopharmacol. 89 (2003) 217-219. doi:10.1016/j.jep.2003.08.006.

[49] G. Kaur, M. Sarwar Alam, M. Athar, Nimbidin suppresses functions of macrophages and neutrophils: relevance to its antiinflammatory mechanisms, Phyther. Res. 18 (2004) 419-424. doi:10.1002/ptr.1474.

[50] S. E. Atawodi, J. C. Atawodi, Azadirachta indica (neem): a plant of multiple biological and pharmacological activities, Phytochem. Rev. 8 (2009) 601-620. doi:10.1007/s11101-009-9144-6.

[51] P. S. Babu, P. S. M. Prince, Antihyperglycaemic and antioxidant effect of hyponidd, an ayurvedic herbomineral formulation in streptozotocin-induced diabetic rats, J. Pharm. Pharmacol. 56 (2004) 1435-1442. doi:10.1211/0022357044607.

[52] M. Ishihara, S. Kishimoto, K. Murakami, H. Hattori, S. Nakamura, T. Saitama, HEPARINOID-BASED BIOMATERIALS AND THEIR APPLICATIONS, Int. J. Pharma Bio Sci. 7 (2016) 218-234.

[53] Y.-J. Chuang, R. Swanson, S. M. Raja, S. T. Olson, Heparin Enhances the Specificity of Antithrombin for Thrombin and Factor Xa Independent of the Reactive Center Loop Sequence, J. Biol. Chem. 276 (2001) 14961-14971. doi:10.1074/jbc.M011550200.

[54] X. Wang, Z. Zhang, Z. Yao, M. Zhao, H. Qi, Sulfation, anticoagulant and antioxidant activities of polysaccharide from green algae Enteromorpha linza, Int. J. Biol. Macromol. 58 (2013) 225-230. doi:10.1016/j.ijbiomac.2013.04.005.

[55] J. Yang, Y. Du, R. Huang, Y. Wan, T. Li, Chemical modification, characterization and structure-anticoagulant activity relationships of Chinese lacquer polysaccharides, Int. J. Biol. Macromol. 31 (2002) 55-62. doi:10.1016/S0141-8130(02)00066-1.

[56] A. L. Bukzem, R. Signini, D. M. dos Santos, L. M. Lião, D. P. R. Ascheri, Optimization of carboxymethyl chitosan synthesis using response surface methodology and desirability function, Int. J. Biol. Macromol. 85 (2016) 615-624. doi:10.1016/j.ijbiomac.2016.01.017.

[57] K. Fujimoto, H. Tadokoro, Y. Ueda, Y. Ikada, Polyurethane surface modification by graft polymerization of acrylamide for reduced protein adsorption and platelet adhesion, Biomaterials. 14 (1993) 442-448. doi:10.1016/0142-9612(93)90147-T.

[58] A. J. G. Jansen, E. C. Josefsson, V. Rumjantseva, Q. P. Liu, H. Falet, W. Bergmeier, S. M. Cifuni, R. Sackstein, U. H. von Andrian, D. D. Wagner, J. H. Hartwig, K. M. Hoffmeister, Desialylation accelerates platelet clearance after refrigeration and initiates GPIbα metalloproteinase-mediated cleavage in mice, Blood. 119 (2012) 1263-1273. doi:10.1182/blood-2011-05-355628.

[59] M. B. Gorbet, M. V. Sefton, Biomaterial-associated thrombosis: roles of coagulation factors, complement, platelets and leukocytes, Biomaterials. 25 (2004) 5681-5703. doi:10.1016/j.biomaterials.2004.01.023.

[60] E. A. Vogler, C. A. Siedlecki, Contact activation of blood-plasma coagulation, Biomaterials. 30 (2009) 1857-1869. doi:10.1016/j.biomaterials.2008.12.041.

[61] E. Salimi, A. Ghaee, A. F. Ismail, M. Karimi, Antithrombogenicity and permeability of polyethersulfone hollow fiber membrane with sulfonated alginate toward blood purification, Int. J. Biol. Macromol. 116 (2018) 364-377. doi:10.1016/j.ijbiomac.2018.04.137.

[62] K. Matsubara, Y. Matsuura, A. Bacic, M.-L. Liao, K. Hori, K. Miyazawa, Anticoagulant properties of a sulfated galactan preparation from a marine green alga, Codium cylindricum, Int. J. Biol. Macromol. 28 (2001) 395-399. doi:10.1016/S0141-8130(01)00137-4.

[63] R. Rupani, A. Chavez, Medicinal plants with traditional use: Ethnobotany in the Indian subcontinent, Clin. Dermatol. 36 (2018) 306-309. doi:10.1016/j.clindermatol.2018.03.005.

[64] D. Soares, A. Godin, R. Menezes, R. Nogueira, A. Brito, I. Melo, G. Coura, D. Souza, F. Amaral, T. Paulino, M. Coelho, R. Machado, Anti-inflammatory and Antinociceptive Activities of Azadirachtin in Mice, Planta Med. 80 (2014) 630-636. doi:10.1055/s-0034-1368507.

[65] M. Abdollahi, S. Damirchi, M. Shafafi, M. Rezaei, P. Ariaii, Carboxymethyl cellulose-agar biocomposite film activated with summer savory essential oil as an antimicrobial agent, Int. J. Biol. Macromol. 126 (2019) 561-568. doi:10.1016/j.ijbiomac.2018.12.115.

[66] R. Salam, J. U. Khokon, S. B. M. T. Mussa, Effect of neem and betel leaf against oral bacteria, Int. J. Nat. Soc. Sci. 1 (2014) 52-57.

[67] R. Tiozzo, M. R. Cingi, D. Reggiani, T. Andreoli, S. Calandra, M. R. Milani, S. Piani, E. Marchi, M. Barbanti, Effect of the desulfation of heparin on its anticoagulant and anti-proliferative activity, Thromb. Res. 70 (1993) 99-106. doi:10.1016/0049-3848(93)90227-F.

[68] M. B. Gorbet, M. V. Sefton, Review: Biomaterial-associated thrombosis: roles of coagulation factors, complement, platelets and leukocytes, in: Biomater. Silver Jubil. Compend., Elsevier, 2004: pp. 219-241. doi:10.1016/B978-008045154-1.50025-3.

[69] L. R. Wang, H. Qin, S. Q. Nie, S. D. Sun, F. Ran, C. S. Zhao, Direct synthesis of heparin-like poly(ether sulfone) polymer and its blood compatibility, Acta Biomater. 9 (2013) 8851-8863. doi:10.1016/j.actbio.2013.07.010.

[70] E. Salimi, A. Ghaee, A. F. Ismail, Improving Blood Compatibility of Polyethersulfone Hollow Fiber Membranes via Blending with Sulfonated Polyether Ether Ketone, Macromol. Mater. Eng. 301 (2016) 1084-1095. doi:10.1002/mame.201600108.

[71] M. Gui, J. Song, L. Zhang, S. Wang, R. Wu, C. Ma, P. Li, Chemical characteristics and antithrombotic effect of chondroitin sulfates from sturgeon skull and sturgeon backbone, Carbohydr. Polym. 123 (2015) 454-460. doi:10.1016/j.carbpol.2015.01.046.

[72] N. A. Alenazi, K. A. Alamry, M. A. Hussein, M. A. Elfaky, A. M. Asiri, Enhanced antifouling and anticoagulant properties of grafted biomolecule polyethersulfone membranes, Polym. Adv. Technol. 30 (2019) 1493-1505. doi:10.1002/pat.4581.

[73] Z. M. Wang, L. Li, B. S. Zheng, N. Normakhamatov, S. Y. Guo, Preparation and anticoagulation activity of sodium cellulose sulfate, Int. J. Biol. Macromol. 41 (2007) 376-382. doi:10.1016/j.ijbiomac.2007.05.007.

[74] F. D. da S. Chagas, G. C. Lima, V. I. N. dos Santos, L. E. C. Costa, W. M. de Sousa, V. G. Sombra, D. F. de Araújo, F. C. N. Barros, E. Marinho-Soriano, J. P. de Andrade Feitosa, R. C. M. de Paula, M. G. Pereira, A. L. P. Freitas, Sulfated polysaccharide from the red algae Gelidiella acerosa: Anticoagulant, antiplatelet and antithrombotic effects, Int. J. Biol. Macromol. 159 (2020) 415-421. doi:10.1016/j.ijbiomac.2020.05.012.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of dissolving blood clots in a subject in need thereof, comprising administering to the subject a therapeutically effective amount of a biocomposite comprising Azadirachta indica leaf powder crosslinked to S-CMC wherein the therapeutically effective amount ranges from 0.04 to 0.2 mg/kg of body weight.

2. The method of claim 1, wherein the subject suffers from myocardial infarction, thromboembolic strokes, deep vein thrombosis, atrial fibriallation and/or pulmonary embolism.

3. The method of claim 2, wherein, prior to the step of forming, the S-CMC is made by reacting CMC and $(N(SO_3Na)_3$ in an aqueous medium.

4. The method of claim 3, wherein the $(N(SO_3Na)_3$ is made by
   reacting sodium nitrite and sodium bisulfate in an aqueous medium.

5. The method of claim 3, wherein the aqueous medium is double distilled water (DDW).

6. The method of claim 4, wherein the aqueous medium is double distilled water (DDW).

* * * * *